(12) United States Patent
Arriaza Muñoz

(10) Patent No.: US 8,489,206 B2
(45) Date of Patent: Jul. 16, 2013

(54) DEVICE FOR NEURONAL THERAPIES

(76) Inventor: Francisco José Arriaza Muñoz, Barcelona (ES)

( * ) Notice: Subject to any disclaimer, the term of this patent is extended or adjusted under 35 U.S.C. 154(b) by 422 days.

(21) Appl. No.: 12/669,313

(22) PCT Filed: Jul. 16, 2007

(86) PCT No.: PCT/ES2007/000430
§ 371 (c)(1),
(2), (4) Date: Jan. 15, 2010

(87) PCT Pub. No.: WO2009/010596
PCT Pub. Date: Jan. 22, 2009

(65) Prior Publication Data
US 2010/0211121 A1    Aug. 19, 2010

(51) Int. Cl.
*A61N 1/00* (2006.01)
*A61B 1/00* (2006.01)

(52) U.S. Cl.
USPC ............ 607/141; 607/53; 607/54; 600/383

(58) Field of Classification Search
USPC ................ 607/53–54, 141; 600/383
See application file for complete search history.

(56) References Cited

U.S. PATENT DOCUMENTS

| 2004/0078064 A1* | 4/2004 | Suzuki ........................ 607/54 |
| 2006/0282130 A1 | 12/2006 | Roy et al. |
| 2007/0043405 A1 | 2/2007 | Rittman |
| 2007/0112392 A1 | 5/2007 | Konchitsky |

FOREIGN PATENT DOCUMENTS

| WO | WO 9749453 | 12/1997 |
| WO | WO 2007064916 | 6/2007 |

OTHER PUBLICATIONS

International Search Report for PCT Application PCT/ES2007/000430, O.E.P.M., Apr. 7, 2008.

\* cited by examiner

*Primary Examiner* — Nicole F Lavert
(74) *Attorney, Agent, or Firm* — Sturm & Fix LLP

(57) ABSTRACT

A device for neuronal therapies comprising a high frequency and/or very high frequency generator (1) functioning by means of coils (11), and associated with two main electrodes (2), which are respectively configured by a core (21) of insulating material with the front end (22) in point form and surrounded by a flexible insulating tubular body (23) extended on the point end (22) of the electrode for separate and safe positioning thereof with respect to the eyes of the patient on which said electrodes (2) are placed in a use operation, in order to cause stimulation of the nervous system and improvement of neuronal transmission by means of the circulation of high frequency currents. Both electrodes (2) are associated with at least one element for support (3) and positioning over the eyes of the patient, based on an element for fastening (4) to the head or a cabin (6).

12 Claims, 2 Drawing Sheets

DEVICE FOR NEURONAL THERAPIES

TECHNICAL FIELD

The present invention refers to a device for neuronal therapy device, mainly to be applied on the human body to create stimulation on the nerve system and to increase neuronal transmission.

CROSS REFERENCE TO RELATED APPLICATIONS

This application is a national stage application of PCT/ES2007/000430 filed Jul. 16, 2007 and is incorporated by reference herein in its entirety.

BACKGROUND INFORMATION

There exists a great variety of therapies applied over human body or animals for stimulating their tissues and organs with therapeutic application or just for toning.

An example of these therapies is the curled sinmerization, in which uses a high frequency or very high frequency generator, based on copper thread bobbins, which is associated to one or more electrodes for its application over patient's body, allowing a soft or low current to pass through the patient's body tissue obtaining a very important stimulation effect.

Nevertheless, for this therapy application, the electrode is mainly metallic, which raises problems for focusing this energy on some body parts.

SUMMARY

The neuronal therapy device, that is the object of this invention, presents different technical particularities, destined to stimulate nerve tissue in a direct way and achieve a improvement on neuronal transmission in diseased in relation with optimum functioning of the nerve system, like fibromialgy and others.

The present invention comprises two electrodes respectively formed by an isolating material core with their front in a shaped form, being this core covered by a tubular isolated body with flexible capacity, like a foam, and prolonged on the shaping end of the core electrode in a safe and distanced way respective to the eye of the patient in which those electrodes will be applied on a regular use, to produce a stimulation on nerve tissue, improving neuronal transmission.

Once coupled the front exit of the tubular flexible body over the eyes, the shaped edge of every electrode core remains in little distance from them, but not touching, with what it is possible to proceed and create a high frequency or very high frequency current circulation directly through the eyes and optic nerves, achieving brain treatment on an effective and direct way.

Both electrodes are in relation with minimum one holding and positioning element over the patient on a safe and comfortable way, due its delicate emplacement.

An isolating core is made of wood or other isolating (insulating) material, in a way that will reduce the restlessness from the patient instead of the application of a metallic electrode. Also produce a discharge effect more comfortable and softer than a metallic one, avoiding patient uncomforting sensations.

In a first construction, a charge bobbin could be placed on the electrode, using a low frequency current from the generator to be multiplied. In a second construction, a charge bobbin is placed on the own generator transmitting high frequency current directly to the electrode's core.

In a basic construction, the electrode holder comprises on a fixing element to the head of the patient like a helmet or an harness and minimum one positioning arm to regulate more or less the distance from the electrodes, so a proper and stable position over the eyes could be achieved.

In a more complex and elaborated construction, the electrode's holder is in association with a therapy cabin, which presents a contact surface for the patient, preferably on a lean position, applying on this surface three additional electrodes in contact with patient's body to achieve a better conduction for high or very high frequency through brain, along the spine and to feet. For example, this additional electrodes are placed on a correspondence with head, back and feet. Those additional electrodes are preferably made on wood or other electrically isolating material, similar than the one on the main electrode's core.

Cabin comprises a partially closing enclosure, preferably covering the body and remaining the head out, for placing the main electrodes holder on patient's face. These electrodes will be also attached to this cover enclosure.

From the existing additional electrodes of the cabin, the electrode to be used on foot's contact, is placed on a variable length position holder to adapt to individual height. This is due that patient position is based on head position respective to main electrodes.

This additional electrode for foot is made on a 2 L shape platforms to make an easy plantar and heel contact for the patient.

In an alternative construction, the cabin includes a subsonic vibration emitter, consistent on a low frequency signal generator and one or more loudspeaker placed on the bottom part of the cabin. This subsonic vibration gives synergic advantages together with high or very high frequency therapies created through main and additional electrodes. Also the cabin will act like a resonant box with subsonic vibration, increasing its benefits on patient's body, producing an important cellular vibration.

The cabin also can use a temperature control for high, regular or low temperature during treatment application.

BRIEF DESCRIPTION OF THE DRAWINGS

To improve on process description, and to enhance the invention characteristics comprehension, attached are a set of drawings with illustrative character and no limitative, with represents as follows.

DETAILED DESCRIPTION OF THE PREFERRED EMBODIMENTS

Figure 1:
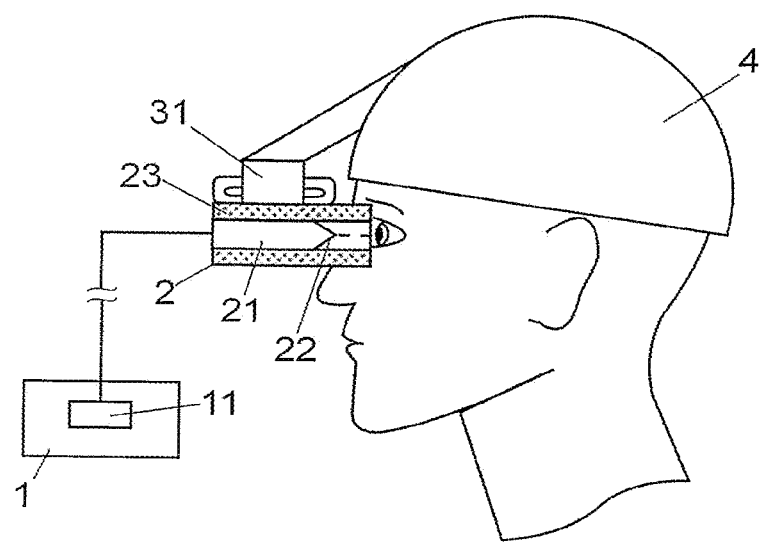
FIG. 1 shows a lateral view about the device in a portable configuration on the head of a patient.
Figure 2:
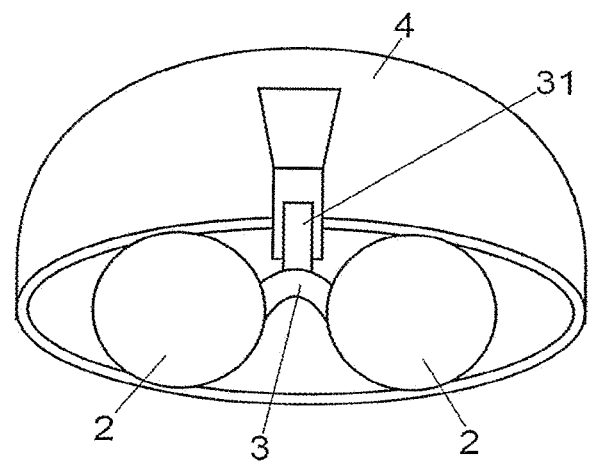
FIG. 2 shows a front view of the device of FIG. 1.

As shown on referenced drawings, the device is basically constituted on a high or very high frequency generator (1) by means of a bobbin(11), associated to two main electrodes (2) to be placed in front of patient's eyes. Each electrode (2) is constituted by wire or other electrically conductive material wound around a core (11) and one core (21), made of wood or other electrically isolating material with one edge (22) on a sharp pointed shape. The mentioned core (21) is connected on it's back edge to the generator (1) with a connection wire throughout the bobbin (11). Over this mentioned core (21) a tubular isolating and flexible body (23) based on a foam material, covering it and prolonged over the sharp edge (22) of the core (21) to protect and make a distance between the point (21) and the end of the flexible body (23).

In a first portable construction, the two electrodes (2) are attached together trough a holding element (3) and a positioning arm (31) with telescopic adjustment on a fixing element (4) to the head, in a helmet configuration, staying the two electrodes (2) in front position pointed to user face, on eye level, getting close or far from them, as needed.

Figure 3:
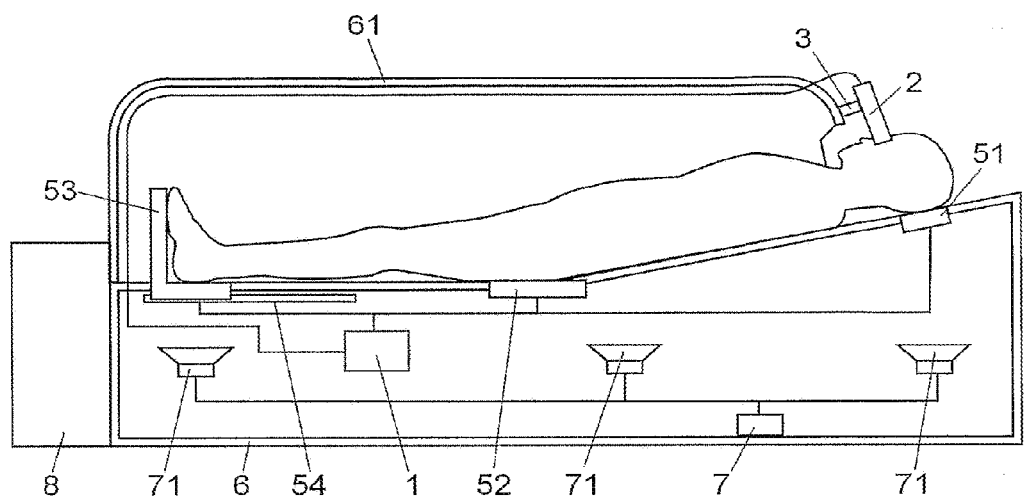
FIG. 3 shows a lateral view with longitudinal cut from device on its complete cabin construction.
Figure 4:
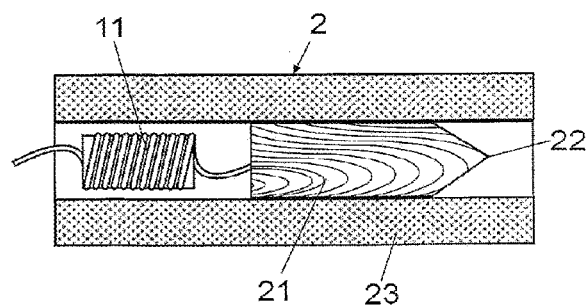
FIG. 4 shows a longitudinal cut view of an alternative creation of an electrode with charge bobbin next to a wood core.

In a more complex construction, the device has one or more additional electrodes (51, 52, 53) (FIG. 3) connected to generator (1). These electrodes (51, 52, 53) are done by isolating material plaques, wood in this case, for its application to the head, back and/or foot of the patient. These electrodes (51, 52, 53) are allocated over a contact surface mainly on a lean position, in a therapy cabin, which includes an enclosure (61) that covers partially patient's body except head, that remains uncovered, finding is this upper part of the lid (61) the main electrodes (2) allocated on an holding element (3) with positioning adjust, included in the lower part of the cabin (6), the high or very high frequency generator(1).

The additional electrode (53) for feet application is based in a two L shaped plaques attached to a (54) length regulating holder to adapt to the user.

The cabin (6) includes inside a low frequency emitter, constituted by a low frequency signal generator (7) and one or more loudspeaker, allocated on the low part so that vibration produced enters in resonance with cabin cavity (6) and produces cellular vibration in the patient. Cabin (6) also presents a thermal regulator (8) inside.

Once described nature of invention, and an example about preferred construction, it's notified that materials, shape, size and position on the described elements could be modified meanwhile essential characteristics of invention claimed below are not modified.

Modifications and substitutions by one of ordinary skill in the art are considered to be within the scope of the present invention, which is not to be limited except by the following claims.

The invention claimed is:

1. A device for neuronal therapies, using a high or very high frequency generator, by means of bobbins, associated to two or more electrodes, the device comprising: two electrodes constituted by a isolating material core with a sharp point edge and covered by a flexible and isolating tubular body, said core of the electrode is made on wood or other electrically insulating material and said flexible and isolating tubular body having a length that is longer than the length of the sharp point edge, for giving a distance and a safe application of the electrodes positioned in a distance in front of eyes of a patient on a standard use, to produce a nerve system stimulation and improving of neuronal transmission using high or very high frequency; and wherein both electrodes are in relation with at least one fixing and positioning element in front of and at the level of the patient's eyes.

2. The device according to claim 1, wherein the bobbins are located in the electrode.

3. The device according to claim 1, wherein the charge bobbin is located in the generator.

4. The device according to claim 1, wherein the holding element of electrodes includes a fixing element on the head of the user and at least one positioning arm to regulate distance for electrodes from the fixing element.

5. The device according to claim 1, wherein the generator is in relation with one or more additional electrodes, disposed on isolating material, to be applied on a head, back and/or foot of the patient.

6. The device according to claim 5, wherein the additional electrodes are made on wood or other isolating materials.

7. The device according to claim 5, wherein the additional electrodes are allocated in a contact surface for the patient, inside a therapy cabin in which is allocated a holding element for the electrodes in an upper position.

8. The device according to claim 7, wherein the cabin has a partially closed cover.

9. The device according to claim 7, wherein one of the additional electrodes is on a length moving holder configured to adapt to a patient's height.

10. The device according to claim 9, wherein one of the additional electrodes is configured by two L shaped plaques for foot support.

11. The device according to claim 7, wherein the cabin includes a subsonic vibration device, constituted by a low frequency signal generator and one or more loudspeaker allocated in a lower part of the therapy cabin.

12. The device according to claim 7, wherein the cabin further includes a temperature control device.

* * * * *